United States Patent [19]
Stabinsky et al.

[11] Patent Number: 5,399,283
[45] Date of Patent: * Mar. 21, 1995

[54] THERMALLY STABLE AND PH STABLE SUBTILISIN ANALOGS AND METHOD FOR PRODUCTION THEREOF

[75] Inventors: Yitzhak Stabinsky, Boulder, Colo.; Mark M. Zukowski, Thousand Oaks, Calif.

[73] Assignee: Amgen Inc., Thousand Oaks, Calif.

[*] Notice: The portion of the term of this patent subsequent to Apr. 3, 2007 has been disclaimed.

[21] Appl. No.: 637,972

[22] Filed: Jan. 9, 1991

Related U.S. Application Data

[63] Continuation of Ser. No. 366,357, Jun. 15, 1989, abandoned, which is a continuation of Ser. No. 193,233, May 6, 1988, abandoned, which is a continuation of Ser. No. 819,241, Jan. 15, 1986, abandoned.

[51] Int. Cl.$^6$ ............... C12N 9/54; C12N 9/56; C11D 17/00
[52] U.S. Cl. ............... 252/174.12; 435/221; 435/222; 435/172.1; 935/14
[58] Field of Search ............... 435/221, 222, 172.3, 435/172.1; 935/14; 252/174.12

[56] References Cited

U.S. PATENT DOCUMENTS

| | | | |
|---|---|---|---|
| 3,732,170 | 5/1973 | Demangeon | 252/95 |
| 3,749,671 | 7/1973 | Gedge, III | 252/89 |
| 3,790,482 | 2/1974 | Jones | 252/525 |
| 3,985,686 | 10/1976 | Barrat | 252/547 |
| 4,052,262 | 10/1977 | Horikoshi et al. | 435/222 |
| 4,760,025 | 7/1988 | Estell et al. | 435/222 |
| 4,771,003 | 9/1988 | Stellwag et al. | 435/221 |
| 4,914,031 | 4/1990 | Zukowski et al. | 435/222 |

FOREIGN PATENT DOCUMENTS

| | | | |
|---|---|---|---|
| 0130756 | 9/1985 | European Pat. Off. | C12N 15/00 |
| WO8304053 | 11/1983 | WIPO | C12P 19/34 |
| 8500817 | 2/1985 | WIPO | . |

OTHER PUBLICATIONS

Stahl et al., *J Bact* 158(2): 411–418, 1984 (May).
Thomas et al., *Nature* 318: 375–376, 1985 (Nov.).
Albertini et al., *J. Bacteriol.*, 162, 1203–1211 (1985).
Beaucage et al., *Tetrahedron Letters*, 22, 1859–1862 (1981).
Birnboim et al., *Nucleic Acid Res.*, 7, 1513–1523 (1979).
Chang et al., *Mol. Gen. Genet.*, 168, 111–115 (1979).
Del Mar et al., *Anal. Biochem.*, 99, 316–320 (1979).
Grunstein et al., *Proc. Nat'l. Acad. Sci. (USA)*, 72, 3961–3965 (1975).
Gounaris et al., *Compt. Rend. Trav. Lab. Carlsberg*, 35, 37 (1965).
Haldenwang et al., *J. Bacteriol*, 142, 90–98 (1980).
Jany et al., *Biol. Chem. Hoppe-Seyler*, 366, 485–492 (1985).

(List continued on next page.)

*Primary Examiner*—Robert A. Wax
*Assistant Examiner*—Keith D. Hendricks
*Attorney, Agent, or Firm*—Marshall, O'Toole, Gerstein, Murray & Borun

[57] ABSTRACT

A mutated subtilisin suitable for admixture to washing compositions and exhibiting substantially improved stability over naturally occurring Bacillus serine proteases is prepared by expressing a modified gene encoding subtilisin in *Bacillus subtilis*. A preferred subtilisin analog product differs from wild-type Bacillus alkaline proteases by having any amino acid, and preferably serine, at position 218 in place of asparagine. The product is preferably produced in a strain of *B. subtilis* which is mutated to block synthesis of endogenous proteases. The method of replacing an Asn or a Gly in an Asn-Gly sequence in order to improve pH and thermal stability may be applied to other sites in subtilisin and to other proteins as well.

9 Claims, 8 Drawing Sheets

OTHER PUBLICATIONS

Kaneda et al., *J. Biochem*, 95, 825–829 (1984).
Lepesant et al., *Microbiology*, in Schlessinger, D. ed. American Society for Microbiology, Washington, D.C., p. 65 (1976).
Lepesant et al., *Molec. Gen. Genet.*, 118, 135–160 (1982).
Mandel et al., *J. Mol. Biol.*, 53, 154 (1982).
Markland et al., *J. Biol. Chem.*, 242, 5198–5211 (1967).
Nedkov et al., *Hoppe-Seyler's Z. Physiol. Chem.*, 364, 1537–1540 (1983).
Norrander et al., *Gene*, 26, 101–106 (1983).
Primrose et al., *Plasmid*, 6, 193–201 (1981).
Saito et al., *Biochim. Biophys. Acta.*, 72, 619–629 (1963).
Sanger et al., *J. Mol. Biol.*, 143, 161–178 (1980).
Smith et al., *J. Biol. Chem.*, 243, 2184–2191 (1968).
Southern, *J. Mol. Biol.*, 98, 503–517 (1975).
Spizizen, *Proc. Nat'l. Acad. Sci. (USA)*, 44, 1072–1078 (1958).
Wong et al., *Proc. Nat'l Acad. Sci. (USA)*, 81, 1184–1188 (1984).
Wright et al., *Nature*, 221, 235–242 (1969).
Young, *J. Gen. Microbiol.*, 129, 1497–1512 (1983).
Zukowski et al., *Proc. Nat'l. Acad. Sci. (USA)*, 80, 1101–1105 (1983).

```
-105
fMet Arg Ser Lys Lys Leu Trp Ile Ser Leu Leu Phe Ala
 GTG AGA AGC AAA AAA TTG TGG ATC AGC TTG TTG TTT GCG

Leu Thr Leu Ile Phe Thr Met Ala Phe Ser Asn Met Ser Ala
TTA ACG TTA ATC TTT ACG ATG GCG TTC AGC AAC ATG TCT GCG

Gln Ala Ala Gly Lys Ser Ser Thr Glu Lys Lys Tyr Ile Val
CAG GCT GCC GGA AAA AGC AGT ACA GAA AAG AAA TAC ATT GTC

Gly Phe Lys Gln Thr Met Ser Ala Met Ser Ser Ala Lys Lys
GGA TTT AAA CAG ACA ATG AGT GCC ATG AGT TCC GCC AAG AAA

Lys Asp Val Ile Ser Glu Lys Gly Gly Lys Val Gln Lys Gln
AAG GAT GTT ATT TCT GAA AAA GGC GGA AAG GTT CAA AAG CAA

Phe Lys Tyr Val Asn Ala Ala Ala Ala Thr Leu Asp Glu Lys
TTT AAG TAT GTT AAC GCG GCC GCA GCA ACA TTG GAT GAA AAA

Ala Val Lys Glu Leu Lys Lys Asp Pro Ser Val Ala Tyr Val
GCT GTA AAA GAA TTG AAA AAA GAT CCG AGC GTT GCA TAT GTG

-1  +1
Glu Glu Asp His Ile Ala His Glu Tyr Ala Gln Ser Val Pro
GAA GAA GAT CAT ATT GCA CAT GAA TAT GCG CAA TCT GTT CCT

10
Tyr Gly Ile Ser Gln Ile Lys Ala Pro Ala Leu His Ser Gln
TAT GGC ATT TCT CAA ATT AAA GCG CCG GCT CTT CAC TCT CAA 20                                                30
Gly Tyr Thr Gly Ser Asn Val Lys Val Ala Val Ile Asp Ser
GGC TAC ACA GGC TCT AAC GTA AAA GTA GCT GTT ATC GAC AGC

40
Gly Ile Asp Ser Ser His Pro Asp Leu Asn Val Arg Gly Gly
GGA ATT GAC TCT TCT CAT CCT GAC TTA AAC GTC AGA GGC GGA 50                                            60
Ala Ser Phe Val Pro Ser Glu Thr Asn Pro Tyr Gln Asp Gly
GCA AGC TTC GTA CCT TCT GAA ACA AAC CCA TAC CAG GAC GGC

70
Ser Ser His Gly Thr His Val Ala Gly Thr Ile Ala Ala Leu
AGT TCT CAC GGT ACG CAT GTA GCC GGT ACG ATT GCC GCT CTT
```

FIGURE 6A

```
                          80
Asn Asn Ser Ile Gly Val Leu Gly Val Ala Pro Ser Ala Ser
AAT AAC TCA ATC GGT GTT CTG GGC GTA GCG CCA AGC GCA TCA 90                                     100
Leu Tyr Ala Val Lys Val Leu Asp Ser Thr Gly Ser Gly Gln
TTA TAT GCA GTA AAA GTG CTT GAT TCA ACA GGA AGC GGC CAA

110
Tyr Ser Trp Ile Ile Asn Gly Ile Glu Trp Ala Ile Ser Asn
TAT AGC TGG ATT ATT AAC GGC ATT GAG TGG GCC ATT TCC AAC 120                                 130
Asn Met Asp Val Ile Asn Met Ser Leu Gly Gly Pro Thr Gly
AAT ATG GAT GTT ATC AAC ATG AGC CTT GGC GGA CCT ACT GGT

140
Ser Thr Ala Leu Lys Thr Val Val Asp Lys Ala Val Ser Ser
TCT ACA GCG CTG AAA ACA GTC GTT GAC AAA GCC GTT TCC AGC

150
Gly Ile Val Val Ala Ala Ala Gly Asn Glu Gly Ser Ser
GGT ATC GTC GTT GCT GCC GCA GCC GGA AAC GAA GGT TCA TCC 160                                      170
Gly Ser Thr Ser Thr Val Gly Tyr Pro Ala Lys Tyr Pro Ser
GGA AGC ACA AGC ACA GTC GGC TAC CCT GCA AAA TAT CCT TCT

180
Thr Ile Ala Val Gly Ala Val Asn Ser Ser Asn Gln Arg Ala
ACT ATT GCA GTA GGT GCG GTA AAC AGC AGC AAC CAA AGA GCT 190                                     200
Ser Phe Ser Ser Ala Gly Ser Glu Leu Asp Val Met Ala Pro
TCA TTC TCC AGC GCA GGT TCT GAG CTT GAT GTG ATG GCT CCT

210
Gly Val Ser Ile Gln Ser Thr Leu Pro Gly Gly Thr Tyr Gly
GGC GTG TCC ATC CAA AGC ACA CTT CCT GGA GGC ACT TAC GGC

220
Ala Tyr Asn Gly Thr Ser Met Ala Thr Pro His Val Ala Gly
GCT TAT AAC GGA ACG TCC ATG GCG ACT CCT CAC GTT GCC GGA 230                                      240
Ala Ala Ala Leu Ile Leu Ser Lys His Pro Thr Trp Thr Asn
GCA GCA GCG TTA ATT CTT TCT AAG CAC CCG ACT TGG ACA AAC

250
Ala Gln Val Arg Asp Arg Leu Glu Ser Thr Ala Thr Tyr Leu
GCG CAA GTC CGT GAT CGT TTA GAA AGC ACT GCA ACA TAT CTT
```

FIGURE 6B

```
              260                                                    270
Gly Asn Ser Phe Tyr Tyr Gly Lys Gly Leu Ile Asn Val Gln
GGA AAC TCT TTC TAC TAT GGA AAA GGG TTA ATC AAC GTA CAA

275
Ala Ala Ala Gln OC
GCA GCT GCA CAA TAA TAGTAAAAAGAAGCAGGTTCCTCCATACCTGCT

TCTTTTTATTTGTCAGCATCCTGATGTTCCGGCGCATTCTC
```

FIGURE 6C

THERMALLY STABLE AND PH STABLE SUBTILISIN ANALOGS AND METHOD FOR PRODUCTION THEREOF

This application is a continuation of application Ser. No. 07/366,357, filed Jun. 15, 1989, which is in turn a continuation of U.S. Ser. No. 07/193,233, filed May 6, 1988; which is in turn a continuation of U.S. Ser. No. 06/819,241, filed Jan. 15, 1986, all now abandoned.

BACKGROUND OF THE INVENTION

The present invention relates in general to thermally stable and pH stable analogs of the enzyme subtilisin and to a method for generating such analogs. In particular, the present invention relates to analogs of Bacillus subtilisin having a substitution for Asn$^{218}$ and to a method for generating such analogs.

The term subtilisin designates a group of extracellular alkaline serine proteases produced by various species of Bacilli. These enzymes are also called Bacillus serine proteases, Bacillus subtilisins or bacterial alkaline proteases.

The Bacillus subtilisin molecules are composed of a single polypeptide chain of either 274 residues (for subtilisin type Carlsberg produced by *Bacillus licheniformis* and for the subtilisin produced by *Bacillus subtilis* strain DY) or 275 residues (for subtilisin type BPN', produced by *Bacillus amyloliquefaciens*, and the aprA gene product of *Bacillus subtilis*). When comparing amino acid sequences of subtilisin from different strains of Bacillus the sequence of subtilisin BPN' is used as a standard. For example, based on an alignment of sequences that gives the highest degree of homology between subtilisin Carlsberg and subtilisin BPN', the serine at the active site of the former is referred to as serine 221, even though it is located at position 220 of the amino acid sequence. On the same basis, position 220 of the amino acid sequence of subtilisin Carlsberg may said to "correspond" to position 221 of subtilisin BPN'. See e.g., Nedkov et al., *Hoppe-Seyler's Z. Physiol. Chem.*, 364, 1537–1540 (1983).

The X-ray structure of subtilisin BPN' [Wright, et al., *Nature*, 221, 235 (1969)] revealed that the geometry of the catalytic site of subtilisin, involving Asp$^{32}$, His$^{64}$ and Ser$^{221}$, is almost identical to that of the active site of mammalian serine proteases (e.g., chymotrypsin) involving the residues Asp$^{102}$, His$^{57}$, and Ser$^{195}$. However, the overall dissimilarities between Bacillus serine proteases and mammalian serine proteases indicate that these are two unrelated families of proteolytic enzymes.

In the family of Bacillus subtilisins complete amino acid sequences are available for four subtilisins: Carlsberg, [Smith, et al., *J. Biol. Chem.*, 243, 2184–2191 (1968)]; BPN' [Markland, et al., *J. Biol. Chem.*, 242, 5198–5211 (1967)]; the aprA gene product [Stahl, et al., *J. Bacteriol.*, 158, 411–418 (1984)]; and DY [Nedkov, et al., supra]. Subtilisin Carlsberg and subtilisin BPN' (sometimes referred to as subtilisin Novo) differ by 84 amino acids and one additional residue in BPN' (subtilisin Carlsberg lacks an amino acid residue corresponding to residue 56 of subtilisin BPN'). Smith, et al., supra. Subtilisin DY is 274 amino acids in length and differs from subtilisin Carlsberg in 32 amino acid positions and from subtilisin BPN' by 82 amino acid replacements and one deletion (subtilisin DY lacks an amino acid residue corresponding to residue 56 of subtilisin BPN'). Nedkov, et al., supra. The amino acid sequence of the aprA gene product is 85% homologous to the amino acid sequence of subtilisin BPN'. Stahl, et al., supra. Thus, it seems that there is an extensive homology between amino acid sequences of serine proteases from different strains of Bacillus. This homology is complete in certain regions of the molecule and especially in those that play a role in the catalytic mechanism and in substrate binding. Examples of such sequence invariances are the primary and secondary substrate binding sites, Ser$^{125}$-Leu$^{126}$-Gly$^{127}$-Gly$^{128}$ and Tyr$^{104}$ respectively and the sequence around the reactive serine (221) Asn$^{218}$-Gly$^{219}$-Thr$^{220}$-Ser$^{221}$-Met$^{222}$-Ala$^{223}$.

Subtilisin molecules exhibit some unique stability properties. They are not completely stable at any pH value although they are relatively resistant to denaturation by urea and guanidine solutions and enzymatic activity is retained for some time even in a solution of 8M urea. In solutions at a pH below 4, subtilisin rapidly and irreversibly loses its proteolytic activity. Gounaris, et al., *Compt. Rend. Tray. Lab. Carlsberg*, 35, 37 (1965) demonstrated that the acid deactivation of subtilisin is not due to a general charge effect and speculated that it is due to other changes in the molecule, such as protonation of histidine residues in the interior, hydrophobic parts of the molecule. In solution at pH above 5, Bacillus serine proteases gradually undergo irreversible inactivation at a rate that increases with temperature and pH. The mechanisms of this inactivation are not fully known but there is evidence indicating that autodigestion is responsible at least in part for enzyme instability at this pH range.

The use of proteases in industrial processes which require hydrolysis of proteins has been limited due to enzyme instability under operational conditions. Thus, for example, the incorporation of trypsin into laundry detergents (e.g., Bio-38, Schnyder; Switzerland) to facilitate removal of proteinaceous stains had a very limited success which was undoubtedly a result of enzyme instability under the washing conditions. It was only about 1960, after the introduction of the use of bacterial alkaline proteases which are more compatible with detergents that proteases came to be widely used in the detergent industry.

For practical reasons many industrial processes are conducted at temperatures that are above the stability range of most enzymes. Therefore, it is reasonable to assume that highly thermostable proteases not only will be advantageous to certain industries such as detergent and hide dehairing, that already require stable proteases, but may be useful in industries that use chemical means to hydrolyze proteins e.g. hydrolysis of vegetable and animal proteins for the production of soup concentrates.

It should be pointed out, however, that although thermal inactivation may be the most important mode of enzyme inactivation, factors other than heat such as extremes of pH, oxygen and denaturing agents may have a determinantal effect on limiting the use of proteases in industrial processes. It is therefore, desirable to obtain proteases that are characterized by improved stability under the operational conditions used in various industries. Such a goal may be accomplished either through searching for new more stable wild-type enzymes or through stabilization of already known existing proteases.

Even though the Bacillus-derived alkaline proteases are more compatible with detergent formulations than were the pancreatic proteases, they are still not ideal in all respects.

Over the past several years there have been major changes in detergent formulations, particularly in the replacement of phosphates with alternate builders and in the development of liquid laundry detergents to meet environmental and consumer demands. These changes create a need for changes in traditional detergent enzymes. More particularly, it has become desirable to employ proteolytic enzymes which possess greater storage stability in liquid laundry formulations as well as stability and activity at broader ranges of pH and temperature.

In one approach to producing modified subtilisins for use in detergent formulations, as disclosed in European Patent Application No. 130,756, mutations in the subtilisin of *Bacillus amyloliquefaciens* (*B. amyloliquefaciens*) at $Tyr^{-1}$, $Asp^{32}$, $Asn^{155}$, $Tyr^{104}$, $Met^{222}$, $Gly^{166}$, $His^{64}$, $Gly^{169}$, $Phe^{189}$, $Ser^{33}$, $Ser^{221}$, $Tyr^{217}$, $Glu^{156}$, and/or $Ala^{152}$ are identified as providing changed stability, altered conformation or as having changes in the "processing" of the enzyme. In this context mutation of $Met^{222}$ to Ala, Cys (which mutant also exhibits a sharper pH optimum than wild type) or Ser assertedly results in improved oxidation stability. Substitution for $Gly^{166}$ with Ala, Asp, Glu, Phe, Hys, Lys, Asn, Arg or Val appears to alter the kinetic parameters of the enzyme. However, none of the mutations are disclosed to provide analogs having greater stability at high temperatures or stability over a broader pH range than the wild type enzyme.

In another approach, it appears that the pH dependence of subtilisin may be altered, as disclosed in Thomas, et al, *Nature*, 318, 375–376 (1985), by changing an Asp to Ser in $Asp^{99}$-$Gly^{100}$ of subtilisin BPN'. This change represents an alteration of a surface charge 14–15 Angstroms from the active site. However, the approach of Thomas, et al. does not provide an indication of improvement where no change in surface charge is made, as is the case where one uncharged residue is substituted for another.

SUMMARY OF THE INVENTION

The present invention provides analogs of Bacillus serine protease products characterized by improved pH and heat stabilities, rendering them especially useful in detergent formulations as well as other processes requiring protease usage. The present invention also provides an industrially feasible recombinant process for preparing the products free of other proteases. Stable analogs according to the present invention are generally characterized by deletion and/or modification and/or replacement of either residue of Asn-Gly sequences present in the protease.

It should be noted that, as employed herein, the term "subtilisin" is used to refer to the mature, secreted form of the enzyme which lacks leader sequences cleaved from the mature enzyme prior to or at secretion.

Presently preferred analogs of a Bacillus subtilisin according to the present invention have an amino acid sequence wherein positions comprising an Asn-Gly sequence in the Bacillus subtilisin do not comprise an Asn-Gly sequence in the analog, and in particular wherein there are fewer Asn-Gly sequences than in the Bacillus subtilisin. Most preferably, a position corresponding to position 218 in the amino acid sequence as set forth in Table 1, does not comprise an asparaginyl residue, but rather comprises a residue of a different amino acid, preferably an amino acid selected from among serine, valine, threonine, cysteine, glutamine and isoleucine. To the extent that replacement of asparagine with certain amino acids may give rise to interference with active site conformation, (e.g., due to steric hindrance which may be introduced by the presence of an aromatic amino acid or changes in tertiary structure such as may be introduced by the presence of a proline) substitution with such amino acids would ordinarily be less preferred. Likewise, to the extent that replacement of asparagine with other amino acids may introduce a charged group (e.g., aspartic acid) into the proximity of the active site, such substitution would be less preferred. Illustrative of a presently preferred embodiment of an analog according to the present invention is a $[Ser^{218}]$-analog of the aprA gene product. Alternative embodiments of analogs within the contemplation of the invention are those wherein $Asn^{109}$ of subtilisin BPN' or of aprA gene product is replaced, preferably by a serine, and wherein glycine residues at positions 110 and/or 219 are replaced by different amino acid residues. In other subtilisins, substitution for Asn at residue 62 or Gly at residue 63 of subtilisins Carlsberg or DY are also comprehended by the present invention.

A nucleic acid according to the present invention has codons encoding a polypeptide analog as described above.

A system for the production of subtilisin according to the present invention comprises a host cell in turn comprising nucleic acid encoding an analog of subtilisin as described above. In such a cell, the nucleic acid encoding the subtilisin analog may be chromosomal or extrachromosomal. The host cell is preferably selected from a strain deficient in secreted proteases, allowing for facile isolation of analog compounds.

A detergent formulation according to the present invention includes an analog of a Bacillus subtilisin having an amino acid sequence comprising an Asn-Gly sequence wherein one or both residues of the Asn-Gly sequence are deleted or are replaced.

A method for improving the thermal and pH stability of subtilisins according to the present invention comprises the step of substituting an amino acid other than asparagine for an asparagine in an Asn-Gly sequence and in particular for the asparagine residue at the position in the amino acid sequence of the subtilisin which corresponds to position 218 in the amino acid sequence as disclosed in Table 1.

BRIEF DESCRIPTION OF THE DRAWINGS

FIG. 6 is a nucleotide and a deduced amino acid sequence for the coding region of the aprA gene of *B. subtilis*.

DETAILED DESCRIPTION

Bacillus serine proteases undergo irreversible inactivation in aqueous solutions at a rate that is largely dependent upon temperature and pH. At pH values below 4 or above 11 the rate of inactivation is very rapid while at pH's of between 4.5 and 10.5 the rate, although much slower, increases as the solution becomes more alkaline. In general, at any pH value, the higher the temperature the faster the rate of subtilisin deactivation.

Figure 1:
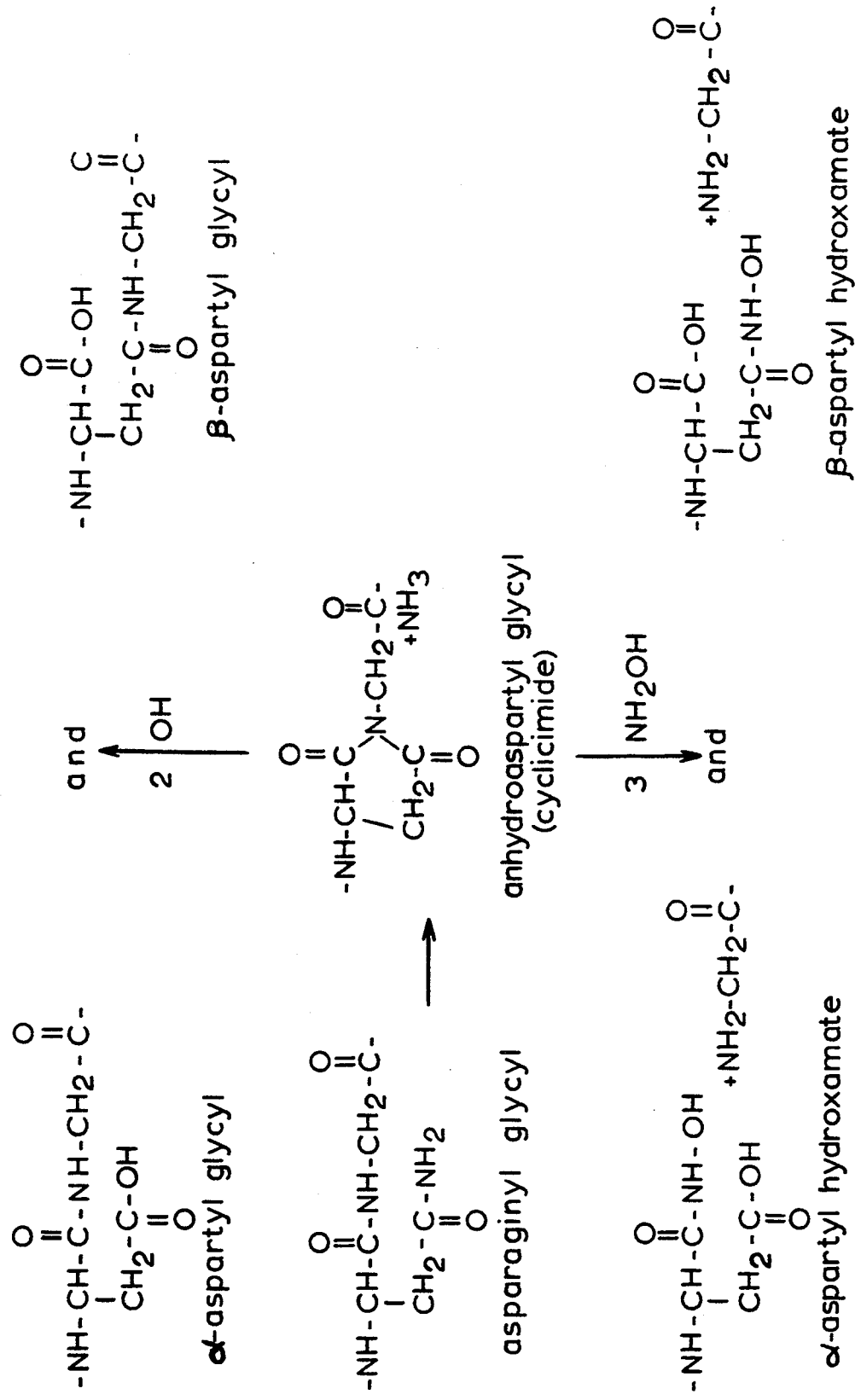
FIG. 1 schematically depicts the cyclization of Asn-Gly residues, such as those found at positions 218 and 219 of subtilisin as set forth in Table 1, to form anhydroaspartylglycine and also depicts base-catalyzed hydrolysis thereof.

A conserved sequence, Asn-Gly, at positions 109–110 and especially at positions 218–219 of Bacillus subtilisins is identified herein as a major factor responsible for the pH instability of these substances. The sequence Asn-Gly in proteins and peptides readily undergoes cyclization under various conditions, to form the cyclic imide anhydroaspartylglycine [Bornstein, et al., *Methods in Enzymol.*, 7, 132–145 (1977)], as illustrated in FIG. 1. This cyclic imide is susceptible to base-catalyzed hydrolysis which preferentially produces a non-native, $\beta$-aspartyl peptide bond. Furthermore, the cyclic imide derived from Asn-Gly may serve as a target for specific cleavage of subtilisin. In fact, the specific cleavage of proteins at Asn-Gly bonds with alkaline hydroxylamine has become a common practice in the preparation of protein fragments for the purpose of amino acid sequencing. [Bornstein, et al., supra]

Formation of a cyclic imide and/or $\beta$-aspartylglycyl peptide at $Asn^{218}$-$Gly^{219}$ of subtilisin is predicted to cause irreversible inactivation of the enzyme. This prediction is based on the close proximity of the unstable Asn-Gly element to a reactive serine located at position 221. A computer analysis of protein structures led to the belief that rearrangement of $Asn^{218}$-$Gly^{219}$ to either anhydroaspartyl glycyl or to $\beta$-aspartyl-glycyl results in a shift of the side-chain of $Ser^{221}$ away from the position it must occupy for the enzyme to be active.

In order to eliminate the unstable element, $Asn^{218}$-$Gly^{219}$, from the subtilisin molecule one can either replace $Asn^{218}$ with any amino acid other than asparagine and/or change $Gly^{219}$ to any amino acid other than glycine. In a like manner, modification of the unstable Asn-Gly element at positions 109–110 is expected to provide benefits in the stability of analogs of the invention.

The observed invariance of $Gly^{219}$ in subtilisins and in subtilisin-like enzymes [e.g. Cucumisin from the melon *Cucumis Melo L.* Var Prince, Kaneda, et al., *J. Biochem.*, 95, 825–829 (1984); and proteinase K, a subtilisin-like serine protease from the fungus *Tritirachium album*, Jany et al., *Biol. Chem. Hoppe-Seyler*, 366, 485–492 (1985)] and the assumption that if $Gly^{219}$ were any residue other than glycine, its side chain might interfere with binding of a substrate to the enzyme, make highly preferred the change of $Asn^{218}$ rather than $Gly^{219}$ for the removal of the unstable $Asn^{218}$-$Gly^{219}$ sequence.

Based on theoretical considerations and on the compilation and analysis of sequencing data, asparagine at position 218 was replaced by serine in the presently preferred embodiment of the present invention described in the following illustrative examples. This selection was based in part on the observation that the amino acid sequence around the reactive serine of cucumisin, a subtilisin-like enzyme from melon fruit, has the sequence Ser-Gly-Thr-Ser-Met (Kaneda, et al., supra).

Proteinase K has the same sequence around the active site. Jany et al., supra. It should be emphasized, however, that the selection of serine as a substitute for $Asn^{218}$ does not preclude achieving the same goal, i.e., elimination of the unstable element $Asn^{218}$-$Gly^{219}$, through replacing asparagine at position 218 with a different amino acid. It is preferred that an uncharged aliphatic amino acid, such as valine, threonine, cysteine, glutamine or isoleucine be substituted for $Asn^{218}$.

Due to their capacity to secrete substantial quantities of proteins and because they are currently used to produce detergent proteases, Bacillus microorganisms represent a preferred host for recombinant production of the [Ser218]-subtilisin according to the present invention. Because most Bacilli secrete alkaline and neutral proteases, it is preferable that mutations be introduced into the endogenous alkaline and neutral protease genes of *B. subtilis* so that the mutated subtilisin may be produced and secreted by *B. subtilis* in a medium free of other proteases. Thus the present invention also provides mutant strains of *B. subtilis* which are blocked with respect to the synthesis of endogenous proteases but which retain the ability to synthesize and secrete subtilisin analogs such as [Ser218]-subtilisin.

As described in greater detail below, it was found that the pH and thermal stability and the stability in detergent formulations of [Ser218]-aprA gene product subtilisin is much greater than that of the wild type aprA gene product subtilisin.

The production of a stable subtilisin analog according to the invention included the following procedures:
1. Isolation of the representative subtilisin gene apr A from *B. subtilis*;
2. Cloning of the apr A gene on a vector which permits utilization of oligonucleotide site-directed mutagenesis to create desired modifications;
3. Site-directed mutagenesis and sequencing of the resulting DNA to confirm the presence of the desired mutation;
4. Construction of an expression vector to direct the synthesis of the mutated enzyme in *B. subtilis*;
5. Construction of mutated *B. subtilis* strains which do not synthesize subtilisin and neutral protease;
6. Isolation of the enzyme in the extra-cellular growth medium and its purification;
7. Assessment of stability and activity characteristics of the isolated product; and
8. Practice of procedures for insertion of the gene coding for the improved enzyme into the chromosome of a *B. subtilis* strain previously mutated to block synthesis of endogenous proteases.

In Example 1, the aprA gene encoding subtilisin is isolated from the *B. subtilis* genome. In Example 2, the aprA gene is subjected to site-directed mutagenesis. In Example 3, an expression vector containing the mutated aprA gene is constructed. In Example 4, two mutant strains of *B. subtilis* which produce no detectable extracellular proteases are constructed. Example 5 describes procedures for integration of a mutated aprA gene into the chromosome of *B. subtilis*. In Example 6, wild-type and mutant aprA subtilisins are isolated and purified. Examples 7 through 10 compare the thermostability of [Ser218] subtilisin to that of wild-type aprA gene product and to that of a commercial BPN' product.

EXAMPLE 1

*B. subtilis* strain QB127 (trpC2 leuA8 sacU$^h$200) [Lepesant, et al., *Molec. Gen. Genet.*, 118, 135–160

(1982)] was obtained from the Bacillus Genetic Stock Center at the Ohio State University, Columbus, Ohio. This strain overproduces extracellular serine and metal proteases, α-amylase and levansucrase relative to isogenic sacU+ strains due to the pleiotropic effect of the sacU$^h$200 mutation [Lepesant, et al., in Schlessinger, D., ed., Microbiology, 1976, American Society for Microbiology, Washington, D.C., p. 65 (1976)] Strain QB127 was thus perceived to be a suitable source of DNA for isolating the aprA gene which codes for subtilisin.

Genomic DNA was isolated from cells of B. subtilis strain QB127 by a published procedure [Saito, et al., Biochim. Biophys. Acta. 72, 619–629 (1963)]. Purified chromosomal DNA was digested to completion with the EcoRI restriction endonuclease.

DNA fragments were resolved on a low-melting point agarose gel by electrophoresis and fragments in the 4.4 to 8.0 kilobase (kb) range were isolated by a standard DNA isolation procedure as recommended by the supplier (Bethesda Research Laboratories, Inc., Gaithersburg, Md.). These fragments were ligated to pCFM936 deposited as No. 53,413 with the American Type Culture Collection, 12301 Parklawn Drive, Rockville, Md., on Jan. 13, 1986, an Escherichia coli (E., coli) "walkaway" plasmid which displays higher copy numbers at elevated temperatures and which confers kanamycin resistance.

The vector was digested with EcoRI and dephosphorylated with calf intestine alkaline phosphatase prior to ligation.

Ligation products were introduced into E. coli C600 (available as A.T.C.C. 23724 from the American Type Culture Collection, 12301 Parklawn Drive, Rockville, Md.) and kanamycin-resistant host cells were selected after overnight incubation on L-agar supplemented with 10 μg/ml kanamycin. Plasmid DNA was amplified by incubating host cells at 42° C. for 4 hours. Colonies were then transferred to nitrocellulose filters and processed by a published procedure referred to as colony hybridization [Grunstein, et al., Proc. Natl. Acad. Sci. (USA), 72, 3961 (1975)].

A probe was used to screen for colonies which harbored the subtilisin gene on pCFM936. The probe [synthesized by the phosphite chemistry method of Beaucage, et al., Tetrahedron Letters, 22, 1859–1862 (1981)] had the nucleotide sequence

5' GCGCAATCTGTTCCTTATGGC 3'  (1)

which corresponds to the amino-terminus of the aprA gene product (Wong, et al., Proc. Natl. Acad. Sci. (USA), 81, 1184–1188 (1984); Stahl, et al., J. Bacteriol., 158, 411–418 (1984). A hybridization temperature of 55° C. was used and 5 positive colonies were identified out of a total of 400. The plasmid DNA from one of the positive colonies was designated pCFM936 apr2.

Plasmid pCFM936 apr2 was digested with EcoRI alone with HindIII alone and with EcoRI and HindIII in combination. Sizes of EcoRI fragments of the subtilisin gene conformed to those described in Stahl, et al., supra, but several otherwise undescribed HindIII sites were discovered. As described in Example 3, two of the HindIII sites were employed for genetic manipulations of the subtilisin gene.

It was determined that a large 6.5 kb EcoRI fragment of B. subtilis QB127 genomic DNA carried the aprA gene, its regulatory sequences and unrelated flanking sequences by verifying that restriction enzyme digests conformed to the results reported by Stahl, et al., supra.

Figure 2:
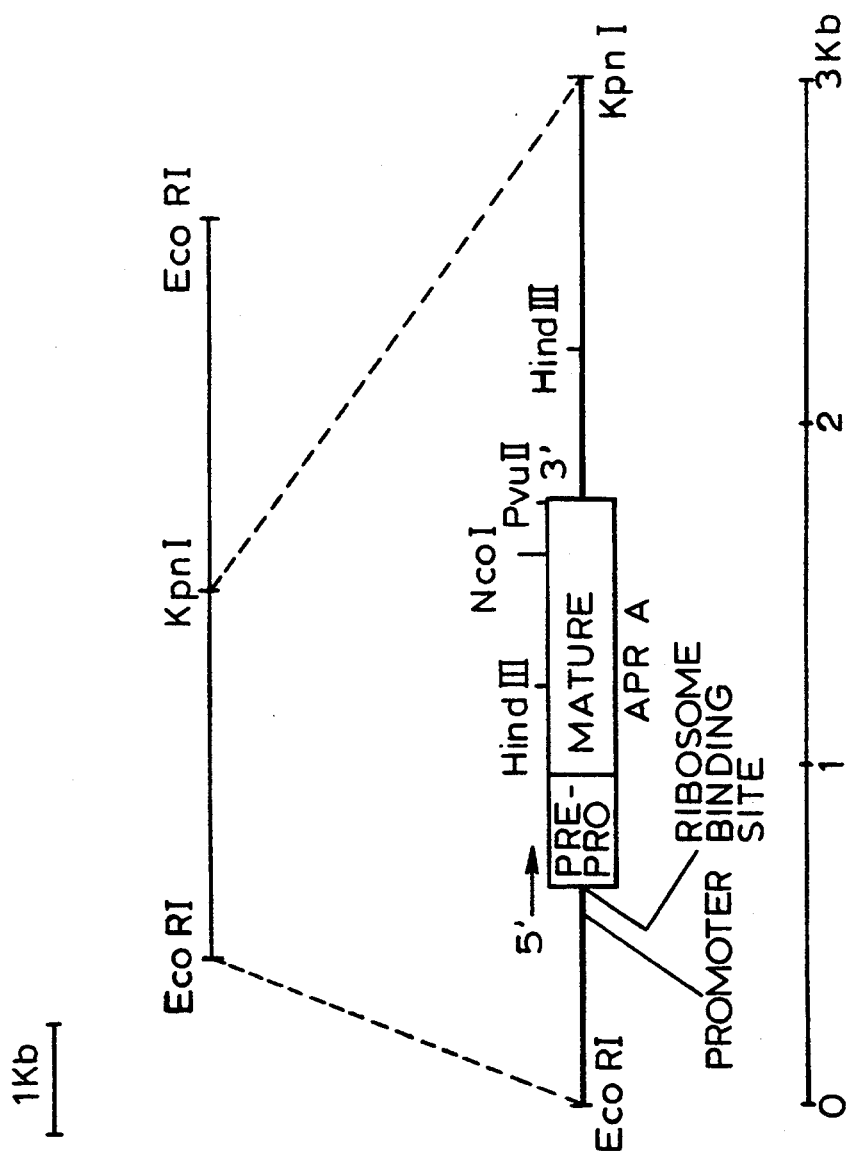
FIG. 2 is a partial restriction map of an aprA gene-containing an EcoRI-KpnI gene fragment of *Bacillus subtilis* (*B. subtilis*) strain QB127 and includes a partial restriction map of the aprA gene and flanking sequences.

This was confirmed by DNA sequencing using the dideoxy chain termination method [Sanger, et al., J. Mol. Biol., 143, 161–178 (1980)]. A 3.0 kb EcoRI to KpnI subfragment of the 6.5 kb EcoRI fragment, as illustrated in FIG. 2, was also found to contain the aprA gene, its regulatory sequences, and unrelated flanking sequences. Although the KpnI-EcoRI fragment is reported to be 2.5 kb in length in the text of Stahl, et al., and in the legend to FIG. 1 therein, comparison of the scale of FIG. 1 and the scaled depiction of the fragment therein reveal that, even in Stahl, et al., the KpnI-EcoRI fragment is substantially larger than 2.5 kb.

A cloning vector for Bacillus host systems, plasmid pAMB11, was constructed as follows. The plasmid pTG402 (Northern Regional Research Laboratories, United States Department of Agriculture, Peoria, Ill., strain number NRRL B-15264) was partially digested with the RsaI restriction endonuclease. Fragments were ligated to M13 mp18 (available from Bethesda Research Laboratories, Gaithersburg, Md. as catalog number 8227SA) which had been previously digested with HincII. Ligation products were introduced into E. coli JM103 (available from Pharmacia, Inc., Piscataway, N.J. as catalog number 27-1545-01) by transformation [Mandel, et al., J. Mol. Biol., 53, 154, (1970)]. Bacteriophage plaques were sprayed with 0.5M catechol (prepared in distilled water) to detect the functional expression of the xylE gene derived from pTG402. The xylE gene encodes catechol 2,3-dioxygenase and is useful for detecting promoters in a variety of organisms. Zukowski, et al., Proc. Natl. Acad. Sci. (USA), 80, 1101–1105 (1983).

The xylE gene was then transferred as a 1.0 kb EcoRI to PstI fragment to the E. coli /B. subtilis plasmid pHV33 (available from the American Type Culture Collection as A.T.C.C. 39217) [Primrose, et al. Plasmid, 6, 193–201 (1981)] obtained from R. Dedonder (Institut Pasteur, Paris, France). The pHV33 plasmid had been previously digested with EcoRI and PstI so that the xylE-containing fragment, when ligated in this region, would inactivate a gene for ampicillin resistance. The resulting plasmid, pAMB21, contains a functional xylE gene in E. coli host cells, but requires the addition of a promoter for xylE to be expressed in B. subtilis host cells. E. coli cells harboring pAMB21 are resistant to tetracycline (15 μg/ml) and chloramphenicol (20 μg/ml) while B. subtilis cells harboring pAMB21 are resistant only to chloramphenicol (5 μg/ml).

The toop transcription termination sequence of bacteriophage lambda was then transferred from plasmid pCFM936 (on a 400 base pair PstI to BglII fragment) to the unique PstI site of pAMB21. A synthetic nucleotide with the sequence 5' GATCTGCA 3' was constructed to join the BglII extremity of the toop fragment to the PstI site of the vector pAMB21. The resulting plasmid was designated pAMB22 and had properties indentical to pAMB21 except for the inclusion of a transcription terminator. The pAMB22 plasmid is useful for detecting strong promoters that are functional in B. subtilis.

Figure 3:
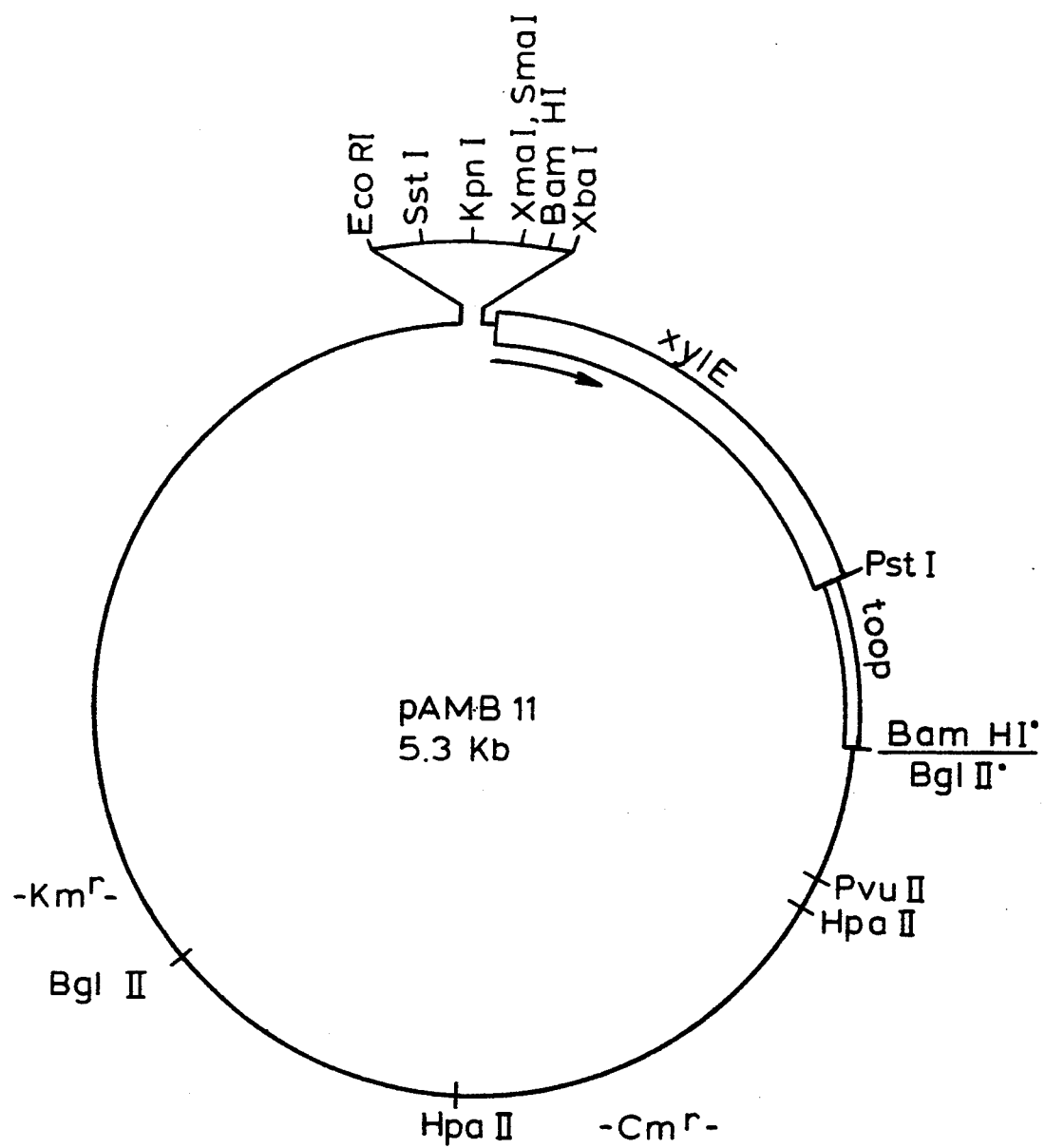
FIG. 3 is a partial restriction map of a plasmid pAMB11.

The 1.4 kb EcoRI to BglII fragment of DNA from pAMB22 that contains xylE and toop was isolated from a low-melting point agarose gel after electrophoresis of restricted fragments. The 1.4 kb piece of DNA was ligated to plasmid pBD64 (available from Bacillus Genetic Stock Center, number 1E22) which had been previously digested with EcoRI and BamHI. The resulting 5.3 kb plasmid, pAMB11, contains the polylinker sequence of M13mp18 (EcoRI, SstI, XmaI, Sma, BamHI and XbaI) upstream of the xylE gene which is followed by toop, as shown in FIG. 3. The pAMB11 plasmid is capable of replicating in *B. subtilis* and confers upon host cells resistance to chloramphenicol (5 μg/ml) and-/or kanamycin (5 μg/ml).

Figure 4:
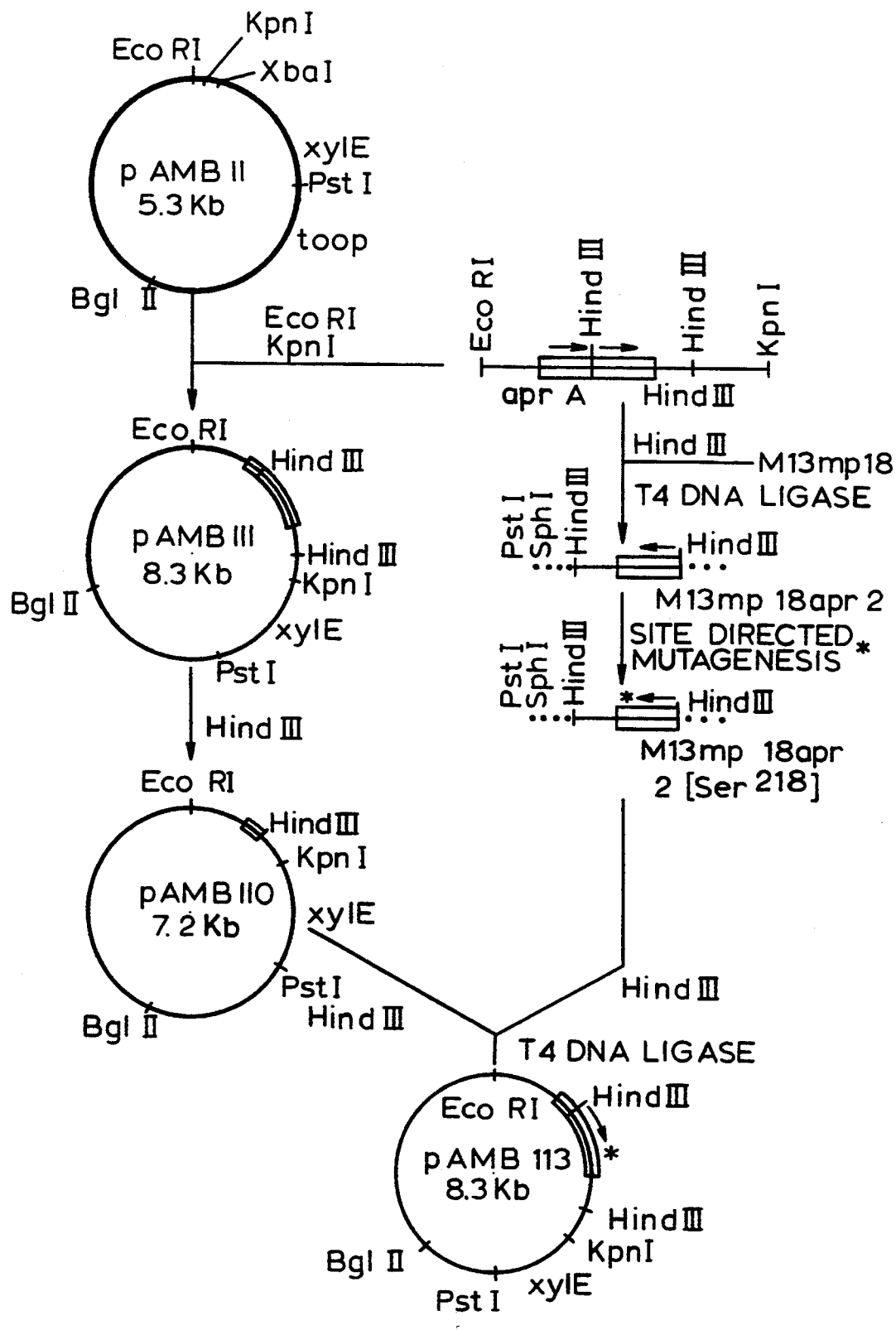
FIG. 4 is a flowchart depicting stages in construction of pAMB113, a plasmid which directs synthesis of $[Ser]^{218}$-subtilisin from *B. subtilis* host cells.

As illustrated in FIG. 4, the purified EcoRI to KpnI fragment containing aprA was cloned onto pAMB11 to form pAMB111. Ligation products were introduced into *B. subtilis* MI112 (arg-15 leuB thr5 recE4) (available from Bacillus Genetic Stock Center as No. 1A423) by the protoplast transformation method [Chang, et al., *Mol. Gen. Genet.*, 168, 111–115 (1979)]. *B. subtilis* MI112 without plasmid DNA is protease-proficient (Prt+ phenotype), but secreted levels of subtilisin are rather low. Chloramphenicol-resistant (Cm$^r$) transformants were transferred onto L-agar plates supplemented with 1.5% (w/v) skim milk and 5 μg/ml chloramphenicol, then incubated at 37° C.

After overnight (approx. 16 hrs.) incubation at 37° C., colonies of MI112 harboring the new recombinant plasmid (designated pAMB111) produced a clear halo surrounding each colony. Halos were formed by the proteolytic action of subtilisin on the casein component of the skim milk medium supplement. MI112 harboring the pAMB11 vector alone had no visible halo after 16 hrs., although a slight halo eventually developed after 40 hrs. at 37° C. Cells carrying pAMB111 were clearly distinguished from cells carrying pAMB11 by a difference in halo size. The cloning of the aprA gene in a fully functional form was thus demonstrated to have led to the high level production and secretion of subtilisin by *B. subtilis*.

EXAMPLE 2

As further illustrated in FIG. 4, the 3.0 kb EcoRI to KpnI genomic fragment, the isolation of which is described in Example 1, was digested with HindIII to produce three fragments: (1) a 1.1 kb EcoRI to HindIII fragment carrying genetic regulatory sequences for aprA gene expression, the "pre-pro" region of the gene required to extracellular export of subtilisin, and the DNA sequence coding for the first 49 amino acids of mature subtilisin; (2) a 1.1 kb HindIII to HindIII fragment carrying DNA sequences coding for amino acids 50 through 275 (carboxyl-terminus) of subtilisin along with a transcription termination sequence and 3' non-coding sequences; and (3) a 0.8 kb HindIII to KpnI fragment containing 3' non-coding sequences.

The 1.1 kb fragment flanked by HindIII sites was cloned to the single HindIII site of bacteriophage M13 mp18 for the purposes of DNA sequencing and site-directed mutagenesis. One of the recombinants, designated M13 mp18 apr2, provided single stranded template DNA required for site-directed mutagenesis of the aprA gene.

The coding region of the aprA gene was sequenced and the results of the sequence are set out in Table 1 below. It should be noted that the specific identity of the initial 5 codons of the leader region is attributable to the report of Stahl, et al., supra, and Wong, et al., supra, of sequence information for the aprA gene, and that there exist codon sequence differences from Stahl, et al., supra, at amino acid positions 84 and 85 which may be the result of sequencing error on the part of the authors of the Stahl, et al. reference or which may be the result of a difference in the nucleotide sequences of the strains employed. Specifically, Stahl, et al., supra, reports a codon GTT (coding for valine) at amino acid position 84 while the codon GTA (also coding for valine) appears in Table 1. Stahl, et al., supra, also reports a codon AGC (coding for serine) at amino acid position 85 as opposed to the codon GCG (coding for alanine) in Table 1.

TABLE 1

```
−105
fMet Arg Ser Lys Lys Leu Trp Ile Ser Leu Leu Phe Ala
GTG AGA AGC AAA AAA TTG TGG ATC AGC TTG TTG TTT GCG

Leu Thr Leu Ile Phe Thr Met Ala Phe Ser Asn Met Ser Ala
TTA ACG TTA ATC TTT ACG ATG GCG TTC AGC AAC ATG TCT GCG

Gln Ala Ala Gly Lys Ser Ser Thr Glu Lys Lys Tyr Ile Val
CAG GCT GCC GGA AAA AGC AGT ACA GAA AAG AAA TAC ATT GTC

Gly Phe Lys Gln Thr Met Ser Ala Met Ser Ser Ala Lys Lys
GGA TTT AAA CAG ACA ATG AGT GCC ATG AGT TCC GCC AAG AAA

Lys Asp Val Ile Ser Glu Lys Gly Gly Lys Val Gln Lys Gln
AAG GAT GTT ATT TCT GAA AAA GGC GGA AAG GTT CAA AAG CAA

Phe Lys Tyr Val Asn Ala Ala Ala Ala Thr Leu Asp Glu Lys
TTT AAG TAT GTT AAC GCG GCC GCA GCA ACA TTG GAT GAA AAA

Ala Val Lys Glu Leu Lys Lys Asp Pro Ser Val Ala Tyr Val
GCT GTA AAA GAA TTG AAA AAA GAT CCG AGC GTT GCA TAT GTG

−1  +1
Glu Glu Asp His Ile Ala His Glu Tyr Ala Gln Ser Val Pro
GAA GAA GAT CAT ATT GCA CAT GAA TAT GCG CAA TCT GTT CCT

10
Tyr Gly Ile Ser Gln Ile Lys Ala Pro Ala Leu His Ser Gln
TAT GGC ATT TCT CAA ATT AAA GCG CCG GCT CTT CAC TCT CAA 20                                    30
Gly Tyr Thr Gly Ser Asn Val Lys Val Ala Val Ile Asp Ser
GGC TAC ACA GGC TCT AAC GTA AAA GTA GCT GTT ATC GAC AGC
```

TABLE 1-continued

```
                                     40
Gly Ile Asp Ser Ser His Pro Asp Leu Asn Val Arg Gly Gly
GGA ATT GAC TCT TCT CAT CCT GAC TTA AAC GTC AGA GGC GGA 50                                  60
Ala Ser Phe Val Pro Ser Glu Thr Asn Pro Tyr Gln Asp Gly
GCA AGC TTC GTA CCT TCT GAA ACA AAC CCA TAC CAG GAC GGC

70
Ser Ser His Gly Thr His Val Ala Gly Thr Ile Ala Ala Leu
AGT TCT CAC GGT ACG CAT GTA GCC GGT ACG ATT GCC GCT CTT

80
Asn Asn Ser Ile Gly Val Leu Gly Val Ala Pro Ser Ala Ser
AAT AAC TCA ATC GGT GTT CTG GGC GTA GCG CCA AGC GCA TCA 90                                     100
Leu Tyr Ala Val Lys Val Leu Asp Ser Thr Gly Ser Gly Gln
TTA TAT GCA GTA AAA GTG CTT GAT TCA ACA GGA AGC GGC CAA

110
Tyr Ser Trp Ile Ile Asn Gly Ile Glu Trp Ala Ile Ser Asn
TAT AGC TGG ATT ATT AAC GGC ATT GAG TGG GCC ATT TCC AAC 120                                 130
Asn Met Asp Val Ile Asn Met Ser Leu Gly Gly Pro Thr Gly
AAT ATG GAT GTT ATC AAC ATG AGC CTT GGC GGA CCT ACT GGT

140
Ser Thr Ala Leu Lys Thr Val Val Asp Lys Ala Val Ser Ser
TCT ACA GCG CTG AAA ACA GTC GTT GAC AAA GCC GTT TCC AGC

150
Gly Ile Val Val Ala Ala Ala Gly Asn Glu Gly Ser Ser
GGT ATC GTC GTT GCT GCC GCA GCC GGA AAC GAA GGT TCA TCC 160                                170
Gly Ser Thr Ser Thr Val Gly Tyr Pro Ala Lys Tyr Pro Ser
GGA AGC ACA AGC ACA GTC GGC TAC CCT GCA AAA TAT CCT TCT

180
Thr Ile Ala Val Gly Ala Val Asn Ser Ser Asn Gln Arg Ala
ACT ATT GCA GTA GGT GCG GTA AAC AGC AGC AAC CAA AGA GCT 190                                 200
Ser Phe Ser Ser Ala Gly Ser Glu Leu Asp Val Met Ala Pro
TCA TTC TCC AGC GCA GGT TCT GAG CTT GAT GTG ATG GCT CCT

210
Gly Val Ser Ile Gln Ser Thr Leu Pro Gly Gly Thr Tyr Gly
GGC GTG TCC ATC CAA AGC ACA CTT CCT GGA GGC ACT TAC GGC

220
Ala Tyr Asn Gly Thr Ser Met Ala Thr Pro His Val Ala Gly
GCT TAT AAC GGA ACG TCC ATG GCG ACT CCT CAC GTT GCC GGA 230                                    240
Ala Ala Ala Leu Ile Leu Ser Lys His Pro Thr Trp Thr Asn
GCA GCA GCG TTA ATT CTT TCT AAG CAC CCG ACT TGG ACA AAC

250
Ala Gln Val Arg Asp Arg Leu Glu Ser Thr Ala Thr Tyr Leu
GCG CAA GTC CGT GAT CGT TTA GAA AGC ACT GCA ACA TAT CTT 260                                 270
Gly Asn Ser Phe Tyr Tyr Gly Lys Gly Leu Ile Asn Val Gln
GGA AAC TCT TTC TAC TAT GGA AAA GGG TTA ATC AAC GTA CAA

275
Ala Ala Ala Gln  OC
GCA GCT GCA CAA TAA TAGTAAAAAGAAGCAGGTTCCTCCATACCTGCT

TCTTTTTATTTGTCAGCATCCTGATGTTCCGGGCGCATTCTC
```

Site-directed mutagenesis was performed by a standard method. Norrander, et al., *Gene*, 26, 101–106 (1983). Single-stranded DNA from M13 mp18 apr2 was annealed to the mutagenic primer

5' GGCGCTTATAGCGGAAC 3'   (2)

which was synthesized by the phosphite chemistry method (Beaucage, et al., supra). The synthetic primer was homologous to codons for amino acids 216 through 220 of subtilisin with the exception of a single base change in the codon for amino acids 218 (AGC instead of AAC). Such a change allowed the mutagenic reaction to substitute a serine codor at position 218 in place of the orginal asparagine codon at this position.

The synthetic primer was annealed to M13 mp18 apr2 DNA at 65° C. before being slowly cooled to room temperature (approx. 22° C.). Polymerization followed for 2 hr. at 15° C. in a reaction mixture which consisted of 12.5 μl of annealed DNA solution, 2.5 μl of 10 mM each dATP, dGTP, dCTP and dGTP, 2.0 μl of 12 mM ATP, 0.1 μl Klenow DNA polymerase, 0.1 μl T4 DNA ligase and 13 μl sterile distilled water. The resulting double-stranded, covalently closed circular DNA was introduced into E. coli JM103 by transfection.

Bacteriophage plaques were then transferred to Gene Screen TM (New England Nuclear, Beverley, Mass.) hybridization membranes. Plaques which contained DNA with the desired base change were identified by hybridization to radioactively labeled ($\gamma$-$^{32}$P) synthetic oligonucleotide (2) used for the mutagenic priming reaction described above. Hybridization was performed at a restrictive temperature (52° C.) so that only DNA carrying the Ser$^{218}$ mutation would hybridize to the synthetic oligonucleotide. The presence of the Ser$^{218}$ mutation in the aprA gene on DNA from a single purified plaque, designated M13 mp18 apr2 [Ser]$^{218}$, was confirmed by DNA sequencing by the method of Sanger, et al., supra.

EXAMPLE 3

In order to express [Ser218]-subtilisin in B. subtilis, a suitable plasmid vehicle was constructed by digesting pAMB111 with HindIII. The 1.1 kb segment carrying most of the aprA gene was deleted by religating HindIII digestion products of pAMB111 at a concentration of approximately 1 μg/ml. This resulted in the formation of pAMB110 as illustrated in FIG. 4. The pAMB110 plasmid carries genetic regulatory sequences for expression of the subtilisin gene, the "pre-pro" region required for secretion of subtilisin, and the DNA sequence coding for the 3' non-coding region of mature subtilisin and the first 49 amino acids of mature subtilisin. Because it is lacking DNA coding for amino acids 50 through 275, pAMB110 does not synthesize subtilisin when introduced into B. subtilis host cells. Subtilisin is synthesized only after insertion of the remainder of a subtilisin gene, either the native DNA sequence or an analog-encoding sequence, such as a sequence encoding [Ser$^{218}$]-subtilisin.

Double-stranded DNA from M13 mp18 apr2 [Ser]$^{218}$ was digested with HindIII. A 1.1 kb fragment carrying the aprA gene segment with the Ser$^{218}$ mutation was then ligated to pAMB110 which had been previously digested with HindIII. Ligation products were introduced into B. subtilis by transformation as in Example 1 above. Ligation of the 1.1 kb HindIII fragment in the correct orientation (as confirmed by DNA sequencing by the method of Sanger, et al. supra) for expression of the mutated gene resulted in the construction of pAMB113, a plasmid which directed synthesis and secretion of [Ser$^{218}$]-subtilisin from B. subtilis host cells.

EXAMPLE 4

Because most Bacilli secrete alkaline and/or neutral proteases into the surrounding growth medium, it is preferable that mutations be introduced into endogenous alkaline and neutral protease genes of B. subtilis to block their synthesis so that mutated subtilisin genes, when introduced into the mutant cell, may produce mutated subtilisins which will then be secreted in a medium free of other proteases likely to interfere with isolation of intact subtilisin analogs. Two mutant B. subtilis strains BZ24 and BZ25, which produce no detectable extracellular proteases, were constructed in the following manner.

Figure 5:
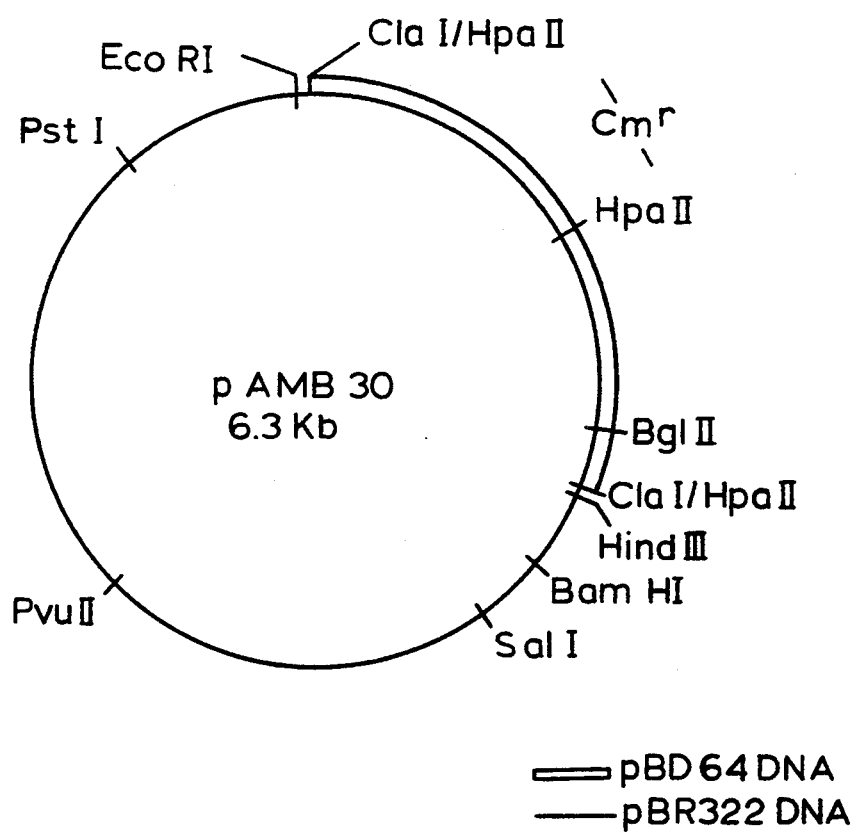
FIG. 5 is a partial restriction map of pAMB30 plasmid.

First, a plasmid vehicle capable of replicating in E. coli , but not in B. subtilis unless integrated into the B. subtilis chromosome by homologous recombination, was constructed as follows. Plasmid pBD64 (Bacillus Genetic Stock Center, Number 1E22) was digested to completion with HpaII to produce three fragments of 2.95 kb, 1.0 kb and 0.75 kb in size. These fragments were then ligated as a mixture to plasmid pBR322 (A.T.C.C. 37017) which previously had been digested with ClaI. Ligation products were introduced into E. coli C600 (available from the American Type Culture Collection as A.T.C.C. 23724) by transformation [Mandel, et al., J. Mol. Biol., 53, 154 (1970)]. Selection was for cells resistant to chloramphenicol (20 μg/ml) and ampicillin (50 μg/ml). Plasmid DNA from 12 transformants was prepared by an alkaline extraction procedure [Birnboim, et al., Nucleic Acids Res., 7, 513–1523 (1979), then digested with HindIII and EcoRI in combination to verify the presence of inserted fragment(s). One such plasmid, designated pAMB30, was found to carry the 1.0 and 0.75 kb HpaII fragments of pBD64 in the ClaI site of pBR322. These fragments contain the chloramphenicol acetyltransferase (cat) gene which is functional in E. coli and B. subtilis. Digestions with BglII and, separately, with Sau3A confirmed the identity and orientation of the cat gene on pAMB30, as illustrated in FIG. 5.

Because pAMB30 lacks an origin of replication sequence which is functional in B. subtilis, it cannot replicate as an autonomous replicon in B. subtilis host cells. On the other hand, pAMB30 contains the pBR322-derived origin of replication which is functional in E. coli, thus the plasmid can be propagated in E. coli host cells. Plasmid pAMB30 is useful in at least 2 ways. First, a fragment of DNA which contains a functional origin of replication in B. subtilis may be detected when cloned onto pAMB30 such that the plasmid will autonomously replicate in the extrachromosomal state. Second, plasmid pAMB30 can integrate into the genome of B. subtilis at a site of homology between the chromosome and B. subtilis DNA cloned onto pAMB30. Such an event has been repeatedly demonstrated in the past [Haldenwang, et al., J. Bacteriol., 142, 90–98 (1980); Young, J. Gen. Microbiol., 129, 1497–1512 (1983)] by using plasmid vehicles similar to, but not identical with, pAMB30.

Plasmid pAMB21 (described in Example 1) was digested with EcoRI and PstI to isolate the xylE gene on a 1.0 kb fragment. The fragment was ligated to pAMB30 which had been previously digested with EcoRI and PstI. Ligation products were introduced into E. coli C600 by transformation. Selection was for chloramphenicol resistant (20 μg/ml) host cells which were sensitive to ampicillin (50 μg/ml) due to the insertion of the xylE fragment of pAMB21 into the structural gene for ampicillin resistance of pAMB30. The resulting plasmid, pAMB30/21, has properties identical to pAMB30 but has, in addition, a functional xylE gene.

Plasmid pAMB110, which carries the aprA gene deleted of a region coding for the latter 226 amino acids of mature subtilisin, was digested with EcoRI and KpnI. The 1.9 kb fragment of B. subtilis DNA containing genetic regulatory sequences for aprA gene expression, "the pre-pro" region, the DNA sequence coding for the first 49 amino acids of mature subtilisin and 3' noncoding sequences was ligated to pAMB30/21 that had been previously digested with EcoRI and KpnI. Ligation products were introduced into E. coli C600 by transformation. Plasmid DNA from several transformants was isolated by the alkaline extraction procedure of Birnboim, et al., supra, and the presence of the inserted 1.9 kb fragment was verified by multiple restriction endonuclease digestions. One such plasmid, designated pAMB301, was retained for further use.

B. subtilis strain BGSC1A274 (Bacillus Genetic Stock Center) carries a mutation at the npr locus and is incapable of producing extracellular neutral protease. The plasmid pAMB301 was integrated into the genome of B. subtilis BGSC1A274 by transformation of competent cells [Spizizen, Proc. Natl. Acad. Sci. (USA), 44, 1072-1078 (1958)]. Selection was for chloramphenicol-resistant (5 μg/ml) host cells which were then transferred by sterile toothpicks to L-agar supplemented with 1.5% (w/v) powdered skim milk and (5 μ/ml) chloramphenicol. Those cells which failed to produce a clear halo surrounding the colony were deficient in the ability to produce extracellular neutral and serine proteases due to the combination of the npr mutation along with the newly introduced aprA mutation. The aprA mutation was a deletion of the latter 226 amino acids of mature subtilisin due to the replacement of the wild-type aprA gene with the deleted version carried on pAMB301. One such strain, designated BZ24, has the Npr⁻ Apr⁻ Cm$^r$ phenotype, thus it produces no detectable extracellular neutral protease nor extracellular alkaline protease and is resistant to chloramphenicol at 5 μg/ml. Southern blotting [Southern, J. Mol. Biol., 98, 503-517 (1975)] was used to confirm the deletion in the aprA gene on the chromosome of B. subtilis BZ24. Cultivation of B. subtilis BZ24 in Antibiotic Medium No. 3 (Penassay Broth, Difco, Detroit, Mich.) in the absence of antibiotic selection for approximately 32 generations led to the isolation of a derivative strain of BZ24 in which the cat gene confering chloramphenicol resistance upon host cells was lost due to its instability in the BZ24 chromosome. Such a phenomenon has been previously observed in similar experiments [Stahl, et al., J. Bacteriol., 158, 411-418 (1984)]. A chloramphenicol-sensitive derivative of BZ24 was designated BZ25. B. subtilis BZ25 has the Npr⁻ Apr⁻ phenotype, thus it produces no detectable extracellular neutral protease nor extracellular alkaline protease. Southern blotting was used to confirm the deletion in the aprA gene on the chromosome of B. subtilis BZ25.

Because B. subtilis BZ25 produces no detectable extracellular neutral protease nor subtilisin, it is a useful host strain for introduction of plasmid DNA, such as pAMB113, for the production of mutated subtilisins which may be secreted into the surrounding growth medium free of other proteases.

B. subtilis BZ25 produces no detectable extracellular proteases when culture supernatants are assayed as described below. B. subtilis BZ25/pAMB113, which is BZ25 that harbors plasmid pAMB113 (introduced by the protoplast transformation method of Chang, et al., supra) produces appreciable quantities of [Ser$^{218}$]-subtilisin when culture supernatants are assayed as described.

EXAMPLE 5

Integration of the [Ser$^{218}$]-subtilisin gene into the chromosome of B. subtilis was believed to provide an efficient way of increasing genetic stability of this mutant gene. Such an approach also alleviates the requirement for chloramphenicol in the fermentation medium which is otherwise needed for application of selective pressure to maintain plasmid DNA in the extra-chromosomol state. Therefore, the [Ser$^{218}$]-subtilisin gene, along with its genetic regulatory sequences and flanking DNA homologous to the B. subtilis chromosome, was isolated from a low melting point agarose gel after electrophoresis of pAMB113 which had been digested with EcoRI and PstI in combination. The 4.0 kb EcoRI to PstI fragment (illustrated in FIG. 4) was then ligated to pAMB30 (illustrated in FIG. 5) which had been digested with EcoRI and PstI in combination. Ligation products were introduced into E. coli HB101 (A.T.C.C. 33694) by transformation. Selection was for cells resistant to chloramphenicol (20 μg/ml). Plasmid DNA from four transformants which met the criteria above were isolated by the alkaline extraction procedure of Birnboim, et al., supra, then digested with EcoRI and PstI in combination. All four plasmids contained the 4.0 kb insert and the 5.6 kb remaining portion of pAMB30. One such plasmid, designated pAMB302, was purified and retained for further use.

Repeated attempts to integrate plasmid pAMB302 into the chromosome of B. subtilis BZ25 by the competence method [Spizizen, supra] were unsuccessful. This may have been due to the failure of BZ25 cells to become competent by the method employed. Therefore, pAMB302 was introduced into B. subtilis BZ25 cells by the protoplast transformation method of Chang, et al., supra. This is believed to be the first demonstration that the protoplast transformation method is successful for obtaining integration of heterologous DNA in Bacillus. This result is particularly significant in that research strains in which integration has been obtained were selected on the basis of transformation by the competence method. Strains which may be unable to become competent, and in particular industrial strains which were not selected on the basis of transformation by the competence method, may be more likely to be unable to become competent.

Selection was for chloramphenicol-resistant cells (5 μg/ml) cells, which were then transferred with sterile toothpicks to L-agar supplemented with 1.5% (w/v) skim milk and 5 μg/ml chloramphenicol. Cells were incubated overnight at 37° C. Clear halos of different diameters were observed around the Cm$^r$ colonies. This indicates that subtilisin was produced and secreted by these cells. An attempt was made to isolate plasmid DNA from eight of these colonies by the alkaline extraction method. No plasmid DNA was detected on agarose gels which were stained with ethidium bromide (1 μg/ml) to visualize DNA after electrophoresis. The absence of extra-chromosomol plasmid DNA in the Cm$^r$ cells which produced subtilisin was a strong indication that pAMB302 had been integrated into the chromosome of B. subtilis.

Several colonies resulting from this experiment were isolated and designated BZ28, BZ29, BZ30, BZ31, BZ32 and BZ33. Each strain was grown overnight at 37° C. with vigorous shaking in brain heart infusion medium (BHI, Difco) supplemented with 5 μg/ml chloramphenicol. Culture supernatants were assayed for subtilisin activity. *B. subtilis* strains BZ28, BZ29, BZ30, BZ31, BZ32 and BZ33 all produced subtilisin and secreted it into the surrounding growth medium, some strains producing more than others. The amount of subtilisin observed in the liquid culture broth was directly proportional to the size of the halo observed on skim milk L-agar plates. Because of the amounts of subtilisin secreted by these cells differed, it was postulated that either multiple copies of pAMB302 were integrated into the chromosome or that gene amplification [Young, *J. Gen. Microbiol.*, 129, 1497–1512 (1983); Albertini, et al., *J. Bacteriol.*, 162, 1203–1211 (1985)] had taken place.

EXAMPLE 6

Wild-type subtilisin, from BZ25/pAMB111, and [Ser$^{218}$]-subtilisin, from BZ25/pAMB113, were isolated and purified as follows. Each culture broth was centrifuged at 15,000 g for 30 minutes and protein in the clear supernatant was precipitated with (NH$_4$)$_2$SO$_4$ (350 g per liter). The precipitate was collected by centrifugation and after trituration with 75% acetone, it was filtered and dried under a vacuum.

In order to further purify the enzyme, the dried precipitate was dissolved in water and the solution was filtered and then dialyzed against 0.02M sodium phosphate buffer at pH 6.3. The dialyzed solution was passed through a column (2.5×0.15 cm) of carboxymethyl cellulose at a rate of 2 ml per minute. After washing the column with 0.02M sodium phosphate (pH 6.3), the enzyme was eluted with the same buffer containing 0.15M NaCl. Peak fractions were pooled and protein from the fractions containing the enzyme, as identified by a color change in a sample of the fraction mixed with succinyl-L-alanyl-L-alanyl-L-prolyl-L-phenylalanyl-p-nitroanilide (Vega Biochemicals), were precipitated by addition of 2.5 volumes of acetone. The precipitate was collected by centrifugation and then dissolved in 0.005M calcium acetate (about 1 ml per 10 mg). The resulting solution was dialyzed at 4° C. against water and then lyophilized.

EXAMPLE 7

Because the present invention relates to the stabilization of Bacillus subtilisin, an analysis of enzyme stability and quantitation thereof was undertaken.

Most enzymes express their biological activity, i.e., catalysis of chemical reactions, only within a narrow range of pH and temperature. Moreover, even under optimal conditions, the enzyme will retain its activity only if its polypeptide chain is folded in a manner that forms the so-called native conformation. The native form of an enzyme is thermodynamically more stable than the denatured or unfolded form by an average of 10–15 kilocalories per mole. Unfolding of the native structure often occurs when the enzyme is exposed to extremes of pH or temperature, or to certain concentrations of chemicals such as detergents, urea and organic solvents. Removal of these denaturing agents often result in spontaneous refolding of the peptide chain to the native form, and in restoration of the original enzyme activity.

Irreversible loss of enzyme activity may occur due to cleavage of the polypeptide chain or due to modification of certain amino acid side chains, especially if these modifications alter the native architecture of the enzymes' active site. Examples of such modifications include the deamidation of asparaginyl and glutaminyl residues, the oxidation of methionyl residues and the hydrolytic cleavage of cysteine to form one residue of thiocysteine and one of dehydroalanine. The present invention provides an additional example in the form of the irreversible inactivation through cyclization of Asn-Gly sequences.

When the enzyme preparation includes several enzymatic forms which inactivate at different rates and/or when the inactivation process occur through a number of mechanisms, the kinetics of inactivation are complicated. However, for most enzyme preparations at a suitable range of pH and temperature, the thermal inactivation follow first-order kinetics, i.e., the residual enzyme activity decreases as a function of time along an exponential decay curve. Under these conditions the half-life ($T_{\frac{1}{2}}$) of the enzyme is independent of the initial enzyme concentration and may be calculated according to:

$$T_{\frac{1}{2}} = \frac{(t_2 - t_1)\ln 2}{\ln A_1 - \ln A_2}$$

in which $A_1$ and $A_2$ are the enzyme activities at times $t_1$ and $t_2$ respectively.

In general, everything else being equal, the half-life of an enzyme in solution is shorter at higher temperatures.

In order to compare the thermostability of the [Ser$^{218}$]-aprA gene product subtilisin to that of wild-type aprA gene product subtilisin and subtilisin BPN' (Sigma), solutions of these enzymes (1 mg/ml) were prepared in 0.1M sodium glycinate buffer at pH 10.0. The solutions were incubated at 52° C. and after various times aliquots (20 μl) were drawn and mixed with 900 μL of 0.2% casein solution in 0.1M Tris buffer at pH 8.30. As a control, the substrate (casein) solution was incubated with 20 μl of enzyme buffer. The hydrolysis of casein at room temperature was terminated after 15 minutes with the addition of 200 μl of 10% trichloroacetic acid. The hydrolysate was separated from the precipitated protein by centrifugation and its ultraviolet (UV) absorbance at 280 nm, as compared to the control, was measured by an 8451A Diode Array Spectrophotometer available from Hewlett Packard. Substrate concentration was such that enzyme activities were directly proportional to the UV absorbances at 280 nm reported in Table 2. In this table the values in parentheses represent percentages of initial enzyme activities. The last column in Table 2 shows the calculated half-life of the three enzymes, and it can be seen that the half-life of the mutated [Ser$^{218}$]aprA gene product is more than three-fold longer than the natural aprA gene product and subtilisin BPN' under the tested conditions.

TABLE 2

| | Thermostability of [Ser$^{218}$]aprA Gene Product vs. Wild-Type aprA Gene Product and Subtilisin BPN' in 0.1M Sodium Glycinate at pH 10.0 | | | | |
|---|---|---|---|---|---|
| | Enzyme Activity After Incubation At 52° C. For: | | | | Half-Life of |
| Protease | 0. Hour | 1 Hour | 2 Hour | 3 Hour | the Enzyme |
| [Ser$^{218}$]aprA | 0.993 (100%) | 0.887 (89%) | 0.738 (74%) | 0.620 (62%) | 4.35 hr |

TABLE 2-continued

Thermostability of [Ser$^{218}$]aprA Gene Product vs. Wild-Type aprA Gene Product
and Subtilisin BPN' in 0.1M Sodium Glycinate at pH 10.0

| Protease | Enzyme Activity After Incubation At 52° C. For: | | | | Half-Life of the Enzyme |
|---|---|---|---|---|---|
| | 0. Hour | 1 Hour | 2 Hour | 3 Hour | |
| Wild-Type aprA | 0.132 (100%) | 0.702 (62%) | 0.437 (38%) | 0.252 (22%) | 1.37 hr |
| Subtilisin BPN' | 0.998 (100%) | 0.596 (60%) | 0.360 (36%) | 0.192 (19%) | 1.25 hr |

EXAMPLE 8

For determination of thermostability of subtilisins in the presence of detergents, the liquid laundry detergent ERA Plus ® (Procter & Gamble) was used after diluting it with water (1:9) and completely inactivating the original protease activity by warming it to 65° C. for 30 minutes. The pH of the resultant detergent solution was 7.50. Using the casein assay and the procedure described in Example 7, the stabilities of [Ser$^{218}$]aprA gene product, wild-type aprA gene product and subtilisin BPN' (Sigma) were tested in the detergent at 45° C. The results are shown in Table 3 in which enzyme activities are expressed as percentages of original enzyme activities. Again, the half-life of the subtilisin analog was on the order of three-fold greater than the natural products under the test conditions.

TABLE 3

Thermostability of [Ser$^{218}$]aprA Gene Product vs.
Wild-Type aprA Gene Product and Subtilisin
BPN' in 0.1M Detergent at pH 7.5

| Protease | Enzyme Activity After Incubation At 45° C. For: | | | | Half-Life of the Enzyme |
|---|---|---|---|---|---|
| | 0 Hour | 0.5 Hour | 1.5 Hour | 3 Hour | |
| [Ser$^{218}$)aprA | 100% | 93% | 82% | 71% | 6.0 hr |
| Wild-Type aprA | 100% | 80% | 54% | 30% | 1.73 hr |
| Subtilisin BPN' | 100% | 84% | 62% | 38% | 2.15 hr |

The above-tabulated results demonstrate that the [Ser$^{218}$]-analog of the aprA gene product exhibits greater stability than the wild type aprA gene product or subtilisin BPN' in ERA Plus ® which, with a pH of 7.5, may be described as a cationic to neutral detergent and which most likely has been formulated to be compatible with inclusion of detergent enzymes. These results do not assure, however, that the [Ser$^{218}$]-aprA gene product will be compatible with all current commercial detergent formulations, e.g., those which have been formulated to the exclusion of detergent enzymes. For example, in preliminary tests with a 2% (w/v) solution of Tide ®, which may be described as an anionic to neutral detergent having a pH of greater than 8.5 and which excludes detergent enzymes in its formulation, the subtilisin BPN' exhibited greater stability than the wild-type and [Ser$^{218}$]-aprA gene products. The [Ser$^{218}$]-aprA gene product in that same test, however, showed greater stability than the wild-type aprA gene product. Although the different relative performance of the [Ser$^{218}$]-aprA gene product and subtilisin BPN' in ERA Plus ® and Tide ® is as yet unexplained, the experimental results suggest that proper formulation of detergent compositions is a prerequisite for optimal performance of enzymes included in such compositions. What has been clearly demonstrated is that the [Ser$^{218}$]-aprA gene product consistently possesses properties superior to those of the wild type aprA gene product, and it is believed that analogs of subtilisins Carlsberg and BPN' according to the present invention will also possess greater stability than the corresponding wild type enzyme.

EXAMPLE 9

Using succinyl-L-alanyl-L-alanyl-L-propolyl-L-phenylalanyl-p-nitroanilide (Vega Biochemicals) as substrate and the rate of increase in absorbance at 405 nm due to release of p-nitroaniline [Del Mar, et al., *Anal. Biochem.*, 99, 316–320, (1979)] to measure enzyme activity, the thermostabilities of [Ser$^{218}$]aprA, wild-type aprA and subtilisin BPN' (Sigma) in 0.1M sodium phosphate buffer at pH 7.5 were determined as follows.

Enzyme solutions of about 0.5 Anson units per liter were incubated at 40° C. and 50° C., and at various times aliquots (20 μl) were drawn and diluted into 180 μl of ice-cold 0.1M sodium phosphate buffer at pH 7.5. 10 μl of the thus diluted sample was mixed with 890 μl of 1 mM succinyl-L-alanyl-L-alanyl-L-prolyl-L-phenylalanyl-p-nitroanilide in 0.1M Tris HCl pH 8.2 and the absorbances at 405 nm were measured every 15 seconds for 5 minutes on a Hewlett Packard, 8451A Diode Array Spectrophotometer. Residual enzyme activities after various incubation times are expressed in Table 4 and Table 5 as percentages of the corresponding initial activities. The procedure was then repeated in 0.1M sodium phosphate buffer at pH 9.0 and the results are set out in Tables 6 and 7.

TABLE 4

Thermostability of [Ser$^{218}$]aprA Gene Product vs.
Wild-Type aprA Gene Product and Subtilisin
BPN' in 0.1M Sodium Phosphate Buffer at pH 7.5

| Protease | Enzyme Activity After Incubation at 40° C. For: | | | | Half Life of the enzyme |
|---|---|---|---|---|---|
| | 0. Min. | 90 Min. | 180 Min. | 270 Min. | |
| [Ser$^{218}$]aprA | 100% | 92% | 87% | 81% | 13.0 hr |
| Wild-Type aprA | 100% | 69% | 48% | 33% | 2.8 hr |
| Subtilisin BPN' | 100% | 48% | 26% | 14% | 1.60 hr |

TABLE 5

Thermostability of [Ser$^{218}$]aprA Gene Product vs.
Wild-Type aprA Gene Product and Subtilisin
BPN' in 0.1M Sodium Phosphate Buffer at pH 7.5

| Protease | Enzyme Activity After Incubation At 50° C. For: | | | | Half Life of the enzyme |
|---|---|---|---|---|---|
| | 0 Min. | 45 Min. | 90 Min. | 135 Min. | |
| [Ser$^{218}$]aprA | 100% | 89% | 81% | 71% | 4.30 hr |
| Wild-Type aprA | 100% | 59% | 35% | 21% | 1.0 hr |
| Subtilisin BPN' | 100% | 34% | 11% | 4% | 0.47 hr |

TABLE 6

Thermostability of [Ser$^{218}$]aprA Gene Product vs. Wild-Type aprA Gene Product and Subtilisin BPN' in 0.1M Sodium Phosphate Buffer at pH 9.0

| Protease | Enzyme Activity After Incubation At 40° C. For: | | | | Half Life of the enzyme |
|---|---|---|---|---|---|
| | 0 Min. | 45 Min. | 90 Min. | 135 Min. | |
| [Ser$^{218}$]aprA | 100% | 96% | 91% | 87% | 11.5 hr |
| Wild-Type aprA | 100% | 79% | 61% | 49% | 2.18 hr |
| Subtilisin BPN' | 100% | 68% | 44% | 29% | 1.25 hr |

TABLE 7

Thermostability of [Ser$^{218}$]aprA Gene Product vs. Wild-Type aprA Gene Product and Subtilisin BPN' in 0.1M Sodium Phosphate Buffer at pH 9.0

| Protease | Enzyme Activity After Incubation At 50° C. For: | | | | | Half Life of the enzyme |
|---|---|---|---|---|---|---|
| | 0 Min. | 20 Min. | 40 Min. | 60 Min. | 80 Min. | |
| [Ser$^{218}$]aprA | 100% | 92% | 85% | 76% | 69% | 2.5 hr |
| Wild-Type aprA | 100% | 61% | 36% | 23% | 14% | 0.47 hr |
| Subtilisin BPN' | 100% | 54% | 31% | 17% | 9% | 0.37 hr |

EXAMPLE 10

In order to test pH stability of the [Ser$^{218}$] analog, the procedure of Example 7 was carried out at pH 4.8 and room temperature and the results are set out in Table 8.

TABLE 8

Stability of [Ser$^{218}$]aprA Gene Product vs. Wild-Type aprA Gene Product in 0.1M Sodium Phosphate Buffer at pH 4.8

| Protease | 0 Hours | 4 Days | Half-life of the enzyme (days) |
|---|---|---|---|
| [Ser$^{218}$]aprA | 100 | 95% | 44.0 |
| Wild-Type aprA | 100 | 47% | 3.7 |

While the present invention has been described in terms of preferred embodiments it is understood that modifications and improvements will occur to those skilled in the art. For example, the sequence Asn-Gly appears at other points in subtilisins, such as at residues 109 and 110 of the aprA gene product and subtilisin BPN' and at residues 62 and 63 of subtilisin Carlsberg and of subtilisin DY. Thus, it is expected that substitution of residues other than Asn and Gly at these respective locations may improve stability as well. Similar improvements in stability are expected for such substitutions made in other enzymes which have the Asn-Gly sequence and in other proteins comprising this sequence. Furthermore, it is expected that a subtilisin analog according to the present invention possesses superior properties to wild type subtilisins in detergent formulations such as those disclosed in, for example, U.S. Pat. Nos. 3,732,170; 3,749,671 and 3,790,482, all of which are incorporated by reference herein.

Moreover, for practical reasons many industrial processes are conducted at temperatures that are above the stability range of most enzymes. Therefore, although detergent applications have been emphasized herein, it is believed that thermostable proteases according to the present invention are not only advantageous to certain industries such as detergent and hide dehairing, which already require stable proteases, but also may be useful in industries that use chemical means to hydrolyze proteins, e.g. hydrolysis of vegetable and animal proteins for the production of soup concentrates.

Therefore, it is intended that the present invention be include all such modifications and improvements as come within the scope of the present invention as claimed.

What is claimed is:

1. An enzymatically active analog of a Bacillus subtilisin, said Bacillus subtilisin having an amino acid sequence comprising an Asn-Gly sequence, said analog having an amino acid sequence wherein an asparaginyl residue in said Asn-Gly sequence of said Bacillus subtilisin is replaced by a residue of a different amino acid.

2. The enzymatically active analog as recited in claim 1 wherein an asparaginyl residue in said Asn-Gly sequence is replaced by a residue of an amino acid from the group consisting of serine, valine, threonine, cysteine, glutamine and isoleucine.

3. The enzymatically active analog as recited in claim 2 wherein said asparaginyl residue in said Asn-Gly sequence is replaced by serine.

4. An enzymatically active analog of a Bacillus subtilisin wherein said enzymatically active analog has an amino acid sequence wherein an asparaginyl residue naturally occurring at a position corresponding to position 218 in the amino acid sequence disclosed in FIG. 6 is replaced by a residue of a different amino acid.

5. The enzymatically active analog as recited in claim 4 wherein an asparaginyl residue at said position is replaced by a residue of an amino acid from the group consisting of serine, valine, threonine, cysteine, glutamine and isoleucine.

6. The enzymatically active analog as recited in claim 5 wherein a seryl residue replaced said asparaginyl residue.

7. The enzymatically active analog as recited in claim 4 wherein said enzymatically active analog is an enzymatically active analog of a naturally occurring Bacillus subtilisin in a strain selected from the group consisting of subtilisin Carlsberg, subtilisin DY, subtilisin BPN' and aprA gene product.

8. The enzymatically active analog as recited in claim 7 wherein all residues except the residue at position 218 comprise amino acid residues as disclosed in FIG. 6.

9. A detergent formulation comprising an enzymatically active analog of a Bacillus subtilisin according to any of claims 1 or 2 through 8.

* * * * *